US009072507B2

(12) United States Patent
Okabe et al.

(10) Patent No.: US 9,072,507 B2
(45) Date of Patent: Jul. 7, 2015

(54) SUCTION PUNCTURE METHOD AND SUCTION PUNCTURE DEVICE

(75) Inventors: Yoshinobu Okabe, Kurume (JP); Ryohei Kaji, Kurume (JP); Yusuke Ishida, Kurume (JP); Makiko Yasumoto, Kurume (JP); Tomohiko Yamaguchi, Kurume (JP); Tomoki Tahira, Kurume (JP); Tomohiko Mamiya, Kawasaki (JP); Kenji Shibaki, Tokyo (JP)

(73) Assignees: Kurume University, Fukuoka (JP); OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 13/616,509

(22) Filed: Sep. 14, 2012

(65) Prior Publication Data
US 2013/0006142 A1 Jan. 3, 2013

Related U.S. Application Data

(63) Continuation of application No. PCT/JP2011/058892, filed on Apr. 8, 2011.

(30) Foreign Application Priority Data

Apr. 8, 2010 (JP) ................ P2010-089331

(51) Int. Cl.
*A61B 10/00* (2006.01)
*A61B 10/02* (2006.01)
(Continued)

(52) U.S. Cl.
CPC ......... *A61B 10/0275* (2013.01); *A61B 10/0283* (2013.01); *A61B 17/3421* (2013.01);
(Continued)

(58) Field of Classification Search
CPC .......................................... A61B 5/00
USPC ..................... 600/562, 564, 565, 566, 567
See application file for complete search history.

(56) References Cited

U.S. PATENT DOCUMENTS 4,651,753 A * 3/1987 Lifton ............... 600/564
4,791,937 A * 12/1988 Wang ............... 600/565
(Continued)

FOREIGN PATENT DOCUMENTS

JP   A-62-064344   3/1987
JP   A-63-068308   5/1988
(Continued)

OTHER PUBLICATIONS

International Search Report dated Jul. 19, 2011 issued in PCT/JP2011/058892.

*Primary Examiner* — Rene Towa
*Assistant Examiner* — May Abouelela
(74) *Attorney, Agent, or Firm* — Scully, Scott, Murphy & Presser, P.C.

(57) ABSTRACT

A suction puncture device includes a puncture needle having an outer tube that has an opening edge of a first front end formed in the shape of a blade, and a stopper member that has a second front end disposed within the outer tube at a position separated from the first front end of the outer tube by a predetermined distance. A sample containing portion is formed between the second front end of the stopper member and the first front end of the outer tube. A ventilation passage is formed around the stopper member within the outer tube, a suction unit is connected to a first base end side of the outer tube, and the suction unit is communicated with and connected to the sample containing portion via the ventilation passage.

9 Claims, 15 Drawing Sheets

(51) Int. Cl.
  *A61B 17/34* (2006.01)
  *A61B 17/32* (2006.01)
  *A61B 1/00* (2006.01)
  *A61B 1/018* (2006.01)
  *A61B 10/04* (2006.01)
  *A61B 17/30* (2006.01)

(52) U.S. Cl.
  CPC . *A61B2017/320064* (2013.01); *A61B 10/0266* (2013.01); *A61B 1/00094* (2013.01); *A61B 1/018* (2013.01); *A61B 17/3478* (2013.01); *A61B 2010/045* (2013.01); *A61B 2017/306* (2013.01)

(56) References Cited

U.S. PATENT DOCUMENTS

| | | | | |
|---|---|---|---|---|
| 4,890,626 | A * | 1/1990 | Wang | 600/565 |
| 5,014,708 | A * | 5/1991 | Hayashi et al. | 600/436 |
| 5,312,327 | A * | 5/1994 | Bales et al. | 604/21 |
| 5,526,822 | A * | 6/1996 | Burbank et al. | 600/567 |
| 5,535,759 | A * | 7/1996 | Wilk | 128/898 |
| 5,685,320 | A * | 11/1997 | Zimmon et al. | 600/567 |
| 5,779,646 | A * | 7/1998 | Koblish et al. | 600/567 |
| 5,810,806 | A * | 9/1998 | Ritchart et al. | 606/45 |
| 5,836,953 | A * | 11/1998 | Yoon | 606/114 |
| 6,059,734 | A * | 5/2000 | Yoon | 600/565 |
| 6,190,330 | B1 * | 2/2001 | Harhen | 600/566 |
| 6,228,039 | B1 * | 5/2001 | Binmoeller | 600/566 |
| 6,623,437 | B2 * | 9/2003 | Hinchliffe et al. | 600/564 |
| 6,770,070 | B1 * | 8/2004 | Balbierz | 606/41 |
| 7,147,607 | B2 * | 12/2006 | Wang | 600/566 |
| 7,186,252 | B2 * | 3/2007 | Nobis et al. | 606/45 |
| 7,192,430 | B2 * | 3/2007 | Truckai et al. | 606/46 |
| 7,204,812 | B2 * | 4/2007 | Wang | 600/566 |
| 7,229,417 | B2 * | 6/2007 | Foerster et al. | 600/562 |
| 7,402,140 | B2 * | 7/2008 | Spero et al. | 600/568 |
| 7,481,817 | B2 * | 1/2009 | Sauer | 606/170 |
| 7,625,397 | B2 * | 12/2009 | Foerster et al. | 606/102 |
| 7,722,549 | B2 * | 5/2010 | Nakao | 600/564 |
| 7,854,706 | B2 * | 12/2010 | Hibner | 600/566 |
| 8,052,614 | B2 * | 11/2011 | Heske et al. | 600/566 |
| 8,282,575 | B2 * | 10/2012 | Tonomura et al. | 600/566 |
| 2004/0162572 | A1 * | 8/2004 | Sauer | 606/170 |
| 2004/0249395 | A1 * | 12/2004 | Mikkaichi et al. | 606/144 |
| 2005/0090763 | A1 * | 4/2005 | Wang | 600/564 |
| 2005/0090764 | A1 * | 4/2005 | Wang | 600/564 |
| 2005/0261581 | A1 | 11/2005 | Hughes et al. | |
| 2006/0116605 | A1 * | 6/2006 | Nakao | 600/566 |
| 2007/0106176 | A1 * | 5/2007 | Mark et al. | 600/566 |
| 2007/0191734 | A1 * | 8/2007 | Grigoryants et al. | 600/564 |
| 2007/0213631 | A1 * | 9/2007 | Kondo et al. | 600/562 |
| 2007/0213632 | A1 * | 9/2007 | Okazaki et al. | 600/562 |
| 2007/0225646 | A1 * | 9/2007 | Tonomura | 604/164.01 |
| 2008/0188767 | A1 * | 8/2008 | Oaki et al. | 600/566 |
| 2009/0069712 | A1 * | 3/2009 | Mulvihill et al. | 600/564 |
| 2009/0131819 | A1 * | 5/2009 | Ritchie et al. | 600/564 |
| 2009/0228034 | A1 * | 9/2009 | Sauer | 606/171 |
| 2010/0217151 | A1 * | 8/2010 | Gostout et al. | 600/565 |

FOREIGN PATENT DOCUMENTS

| | | |
|---|---|---|
| JP | A-63-068309 | 5/1988 |
| JP | A-03-073113 | 7/1991 |
| JP | A-03-083509 | 8/1991 |
| JP | A-08-117232 | 5/1996 |
| JP | A-8-206118 | 8/1996 |
| JP | A-11-225951 | 8/1999 |
| JP | A-11-226024 | 8/1999 |
| JP | T-11-514564 | 12/1999 |
| JP | A-2001-149374 | 6/2001 |
| JP | A-2001-170059 | 6/2001 |
| JP | A-2001-231782 | 8/2001 |
| JP | T-2001-515372 | 9/2001 |
| JP | A-2005-52408 | 3/2005 |
| JP | A-2005-58431 | 3/2005 |
| JP | A-2005-73798 | 3/2005 |
| JP | A-2005-349121 | 12/2005 |
| JP | A-2007-20868 | 2/2007 |
| JP | A-2008-500139 | 1/2008 |
| WO | WO 97/20504 | 6/1997 |
| WO | WO 2007/013130 A1 | 2/2007 |

* cited by examiner

SUCTION PUNCTURE METHOD AND SUCTION PUNCTURE DEVICE

This application is a continuation application based on a PCT Patent Application No. PCT/JP2011/058892, filed Apr. 8, 2011, whose priority is claimed on Japanese Patent Application No. 2010-089331, filed in Japan on Apr. 8, 2010.

The contents of both the PCT Application and the Japanese Application are incorporated herein by reference.

BACKGROUND OF THE INVENTION

1. Field of the Invention

The present invention relates to a suction puncture method and a device using the same that samples a tissue or the like as a testing sample from a predetermined part of a body parts or organ to be examined in a living body under the guide of an ultrasonic image, an optical endoscope image, an ultrasonic endoscope image, or the like, in tissue testing or the like of the body part or organ, and more specifically, relates to a suction puncture method and a suction puncture device that can safely collect the tissue or the like of a predetermined part by simple manipulation, and can collect a tissue of any size without crushing the tissue.

2. Description of Related Art

Generally, the method of collecting a tissue or the like from an internal body part or the like that is a target to be examined includes a method of puncturing and collecting the target body part or the like with a collecting needle under the guide of an ultrasonic image, an optical endoscope image, or an ultrasonic endoscope image. For example, the method of performing collection under the guide of an ultrasonic endoscope image performs collection using the collecting needle attached to an endoscope. That is, this method punctures the inside of a target body part or organ with the collecting needle (puncture needle) while specifying a predetermined part on the basis of the projected image by an ultrasonic endoscope, and collects a tissue or the like with this puncture needle.

In the conventional technique, the above collection method includes a so-called suction method (for example, refer to Japanese Unexamined Patent Application, First Publication No. S08-117232) that inserts a puncture needle into a predetermined position (for example, a tumor part or the like) of a target body part or the like, and decompresses the inside of the puncture needle by suctioning using a suction device, such as an injector, and suctions a tissue into the inside of the needle, and a so-called Trucut method (for example, refer to Published Japanese Translation No. 2001-515372 of the PCT International Publication) for pinching a tissue into the puncturing puncture needle.

The puncture needle to be used for the suction method includes an outer tube (51) for collection inserted into an ultrasonic endoscope so as to be able to advance and retreat, and an inner rod (52) inserted into the inside of the outer tube so as to be able to advance and retreat, for example as shown in FIG. 6. The outer tube (51) can be advanced from the front end of that ultrasonic endoscope by manual operation on the base end (external terminal) side of the ultrasonic endoscope. Additionally, the inner rod (52) can be advanced from the front end of the outer tube (51) and can also be extracted and removed from the base end side of the outer tube (51), by manual operation on the base end side of the outer tube (51). Additionally, a suction device, such as an injector, can be attached to the base end side of the outer tube (51), and the inside of the outer tube (51) is brought into negative pressure by manipulating this suction device.

In the suction method, the puncture needle (50) is manipulated as follows.

First, as shown in FIG. 7A, the puncture needle (50) is guided to, for example, the vicinity of a target body part (53) in a state the inner rod (52) is inserted into the outer tube (51) for collection under the guide of the ultrasonic endoscope. At this time, the inner rod (52) is held at a position as closer to the front end portion as possible slightly inward from a front end port of the outer tube (51). The inner rod (52) is provided to prevent tissues other than the target part or the like from entering the outer tube (51) and to avoid contamination caused by mixing of tissues other than the target part as much as possible, when the puncture needle (50) punctures the target body part (53).

Next, as shown in FIG. 7B, for example, a predetermined diseased part of the body part (53) is punctured by the puncture needle (50) in this state. If the puncture needle (50) reaches the predetermined part, tissues (57) other than the target part, such as an alimentary canal mucosa (56) may enter the inside of the front end of the outer tube (51). Thus, as shown in FIG. 7C, the inner rod (52) is pushed out further forward than the tip of the puncture needle (50), and the other tissues (57) accumulated inside the outer tube (51) are discharged.

Next, the inner rod (52) is extracted from the base end side of the outer tube (51), and as shown in FIG. 7D, the suction device (54), such as an injector, is connected to the base end (external terminal) side of the outer tube (51) so as to bring the inside of the outer tube (51) into negative pressure. With this negative pressure being applied, as shown in FIG. 7E, the tip of the puncture needle (50) is advanced and retreated (stroke) 15 to 20 times within the predetermined part of the target body part (53). Thereby, a tissue of the predetermined part is suctioned and collected into the outer tube (51). Thereafter, suction using the negative pressure is released, and the suction device (54) is extracted. Then, as shown in FIG. 7F, the puncture needle (50) is rapidly extracted from the ultrasonic endoscope (55), the collected substance (58) of cells or tissue pieces collected within the outer tube (51) is taken out to a laboratory dish, and is used as a testing sample.

On the other hand, for example, as shown in FIG. 8, a puncture needle (60) to be used for the Trucut method includes an outer tube for collection (62) that is contained within a catheter sheath (61) and formed in the shape of a blade, and an inner needle (63) that is inserted into the outer tube so as to be able to advance and retreat, and a tray portion (64) for containing a sample is recessed in the vicinity of the tip of the inner needle (63).

In the Trucut method, the puncture needle (60) is manipulated as follows.

First, as shown in FIG. 9A, the tray portion (64) of the inner needle (63) is placed in a state where the tray portion comes out of the front end of the outer tube (62) within the catheter sheath (61), and the outer tube (62) and the inner needle (63) are fixed together at a position where the tip of the inner needle (63) does not come out of the front end of the catheter sheath (61). In this state, the puncture needle is guided to the vicinity of the target body part (65). Reference numeral (66) represents organs, such as an alimentary canal mucosa, other than the target body part.

Next, as shown in FIG. 9B, the puncture needle (60) punctures a target part under the guide of the ultrasonic endoscope. Thereby, the tissue of the target part enters the tray portion (64). In this state, as shown in FIG. 9C, with the inner needle (63) being fixed, the outer tube (62) is pushed out to the front end side, a target tissue is cut off by a front end edge of the outer tube, the inner needle (63) is contained within the outer tube (62). Thereafter, as shown in FIG. 9D, the outer tube (62) in which the inner needle (63) is contained is returned to the inside of the catheter sheath (61), the puncture needle (60) is extracted from the ultrasonic endoscope, and the collected tissue (67) is taken out to a laboratory dish from the tray portion (64).

SUMMARY OF THE INVENTION

According to a first aspect of the present invention, a suction puncture device includes: a puncture needle having an outer tube that has an opening edge of a first front end formed in the shape of a blade, and a stopper member that has a second front end disposed within the outer tube at a position separated from the first front end of the outer tube by a predetermined distance, a sample containing portion is formed between the second front end of the stopper member and the first front end of the outer tube, a ventilation passage is formed around the stopper member within the outer tube, a suction unit is connected to a first base end side of the outer tube, and the suction unit is communicated with and connected to the sample containing portion via the ventilation passage.

According to a second aspect of the present invention, in the suction puncture device of the first aspect, the puncture needle includes an inner rod that replaces with the stopper member and is arranged within the outer tube, and the inner rod is capable of being switched to a closing posture in which the inner rod is located near the second front end of the outer tube inside the outer tube, and a removal posture in which the inner rod is pushed out outward from the second front end of the outer tube.

According to a third aspect of the present invention, in the suction puncture device according of the second aspect, the inner rod serves as the stopper member.

According to a forth aspect of the present invention, in the suction puncture device of any one of the first aspect to third aspect, the outer tube has a connecting portion including a stopper member insertion port and a suction unit communication port on the first base end side, the stopper member insertion port allows the stopper member to be airtightly inserted thereinto, and the suction unit communication port allows the suction unit to be airtightly connected thereto.

According to a fifth aspect of the present invention, in the suction puncture device of the forth aspect, the stopper member insertion port is capable of fixing and holding a second base end side of the stopper member at arbitrary position.

According to a sixth aspect of the present invention, in the suction puncture device according of the forth aspect, the connecting portion is formed separately from the outer tube, and includes an outer tube connection port which is capable of being airtightly connected with the first base end portion of the outer tube.

According to a seventh aspect of the present invention, in the suction puncture device according of the fifth aspect, the connecting portion is formed separately from the outer tube, and includes an outer tube connection port which is capable of being airtightly connected with the first base end portion of the outer tube.

According to an eighth aspect of the present invention, the suction puncture device of any one of the first aspect to the seventh aspect further includes an opening and closing unit which is arranged between the suction unit and the first base end side of the outer tube, and is capable of opening and closing the communication between the suction unit and the ventilation passage.

According to a ninth aspect of the present invention, in the suction puncture device of any one of the first aspect to the eighth aspect, the suction unit includes a pressure adjusting unit capable of adjusting a pressure change in the sample containing portion.

According to a tenth aspect of the present invention, in the suction puncture device of any one of the first aspect to the ninth aspect, the puncture needle is covered with a protective tube.

According to an eleventh aspect of the present invention, in the suction puncture device of any one of the first aspect to the tenth aspect, the puncture needle is mounted within the endoscope so as to be able to advance and retreat.

According to a twelfth aspect of the present invention, in the suction puncture device of the eleventh aspect, the endoscope is an ultrasonic endoscope.

According to a thirteenth aspect of the present invention, in the suction puncture device of the forth aspect, the stopper member has a larger-diameter portion of which the radial dimension is enlarged, at a portion thereof in the longitudinal direction, an annular elastic body is arranged in the stopper member insertion port so as to allow the stopper member to be inserted through the insertion port, and the stopper member insertion port is airtightly closed in a state where the larger-diameter portion is located within a hole of the elastic body.

According to a fourteenth aspect of the present invention, the suction puncture device of the forth aspect further includes an union joint that is screw-fitted into the stopper member insertion port, and an annular elastic body that is arranged between the stopper member insertion port and the union joint and is compressed by the screw fitting, and a tapered portion is formed at the stopper member insertion port so that the internal diameter thereof becomes gradually smaller from an opening end.

DETAILED DESCRIPTION OF THE INVENTION

An embodiment of the invention will be described below on the basis of the drawings.

Figure 1:
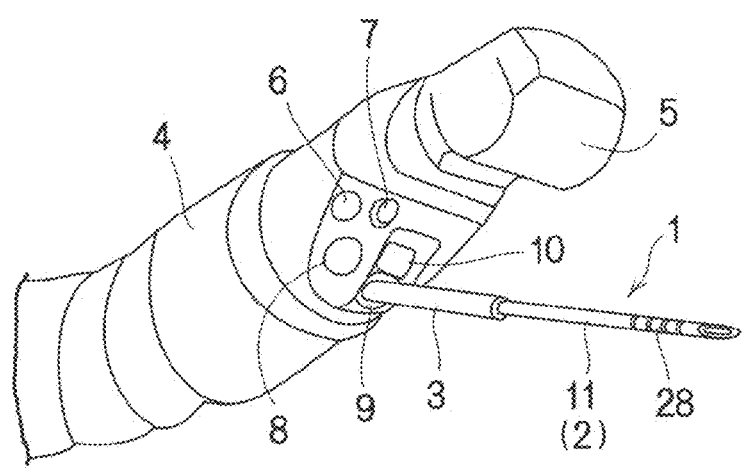
FIG. 1 is an appearance view of a state where a tip portion of a puncture needle is advanced from an ultrasonic endoscope, showing an embodiment of the present invention.

As shown in FIG. 1, a suction puncture device (1) of one embodiment of the present invention includes a puncture needle (2), and is mounted within an ultrasonic endoscope (4) so as to be able to advance and retreat in a state where the suction puncture device is covered with a protective tube (3). The front end of the ultrasonic endoscope (4) is provided with a probe (5), a light guide (6), an air supply and water supply nozzle (7), an objective lens (8), a forceps port (9), and a forceps erection base (10), and the puncture needle (2) is configured so that the front end thereof can be advanced from the forceps port (9).

Figure 2:
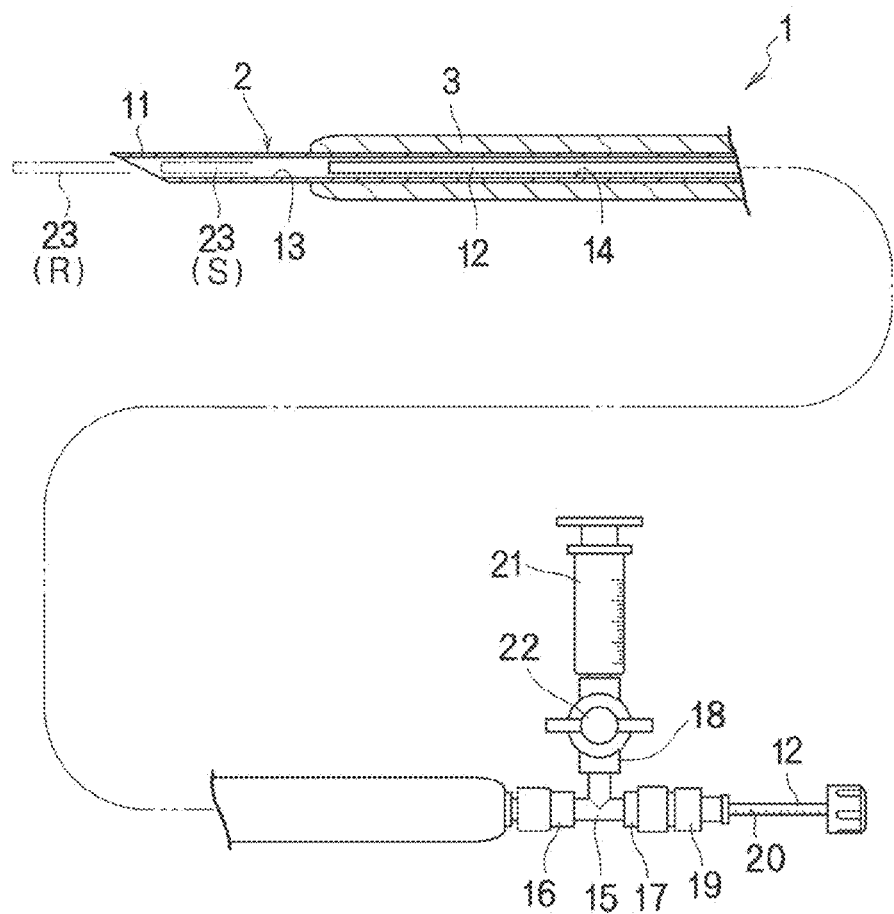
FIG. 2 is an appearance view of the embodiment of the present invention with an intermediate portion of a suction puncture device.

As shown in FIG. 2, the puncture needle (2) has an outer tube (11), and a stopper member (12) that has a front end portion disposed within the outer tube (11) at a position separated from the front end (first front end) of the outer tube (11) by a predetermined distance. The outer tube (11) has an opening edge of a front end formed in the shape of a blade. A sample containing portion (13) is formed between the front end of the outer tube (11) and the front end (second front end) of the stopper member (12). Additionally, a ventilation passage (14) is formed around the stopper member (12) within the outer tube (11). The passage cross-sectional area of the ventilation passage (14) is made greatly smaller than the radial cross-sectional area of the inner space of the outer tube (11).

A connecting portion (15) is attached to the base end (external terminal, first base end) side of the outer tube (11). The connecting portion (15) includes an outer tube connection port (16), a stopper member insertion port (17), and a suction device communication port (18), and a base end portion of the outer tube (11) is airtightly and detachably connected to the outer tube connection port (16). A stopper member (12) can be airtightly inserted into the stopper member insertion port (17), and the stopper member (12) is fixed and held at any predetermined position by a union joint (19) attached to the stopper member insertion port (17).

If an inside front end of the stopper member (12) arrives at a predetermined position within the outer tube (11), typically, a base end portion of the stopper member (12) protrudes further outward than the stopper member insertion port (17). Scales (20) corresponding to the distance from the front end of the outer tube (11) to the inside front end of the stopper member (12) are given to an outer peripheral surface of the protruding base end portion if needed. By adjusting the insertion location of the stopper member (12) with reference to the scales (20), the length (volume) of the sample containing portion (13) formed between the front end of the outer tube (11) and the inside front end of the stopper member (12) is set as a predetermined value.

For example, an injector type suction device (21) serving as a suction device is airtightly connected to the suction device communication port (18) via a cock (22) that is an opening and closing device. Accordingly, the suction device (21) is connected to and made to communicate with the sample containing portion (13) via the ventilation passage (14). The communication between the suction device (21) and the ventilation passage (14) can be opened and closed by the cock (22).

An inner rod (23) can be arranged within the outer tube (11) so as to be replaced for the stopper member (12), as shown by a virtual line of FIG. 2. The inner rod (23) can be switched to a closing posture (S) in which the inner rod is located near the front end inside the outer tube (11), and a removal posture (R) in which the inner rod is pushed out outward from the front end of the outer tube (11).

Next, the above respective members will be described in detail.

(1) Outer Tube (Puncture Needle)

Since the outer tube (11) punctures a body tissue or an organ to take out a tissue sample, the front end thereof is obliquely cut out, and the peripheral edge of the opening thereof is formed in the shape of a cutter (blade). Moreover, dimensions, such as an external diameter, are set in very general ranges in consideration of the influence on a human body, and the puncture needle used in the conventional suction method or the like may be used from this viewpoint. For example, although the specification of the size varies according to a target body part or the like, generally, 19G (the external diameter of 1.06 mm and the internal diameter of 0.70 mm), 22G (the external diameter of 0.71 mm and the internal diameter of 0.41 mm), 25G (the external diameter of 0.51 mm and the internal diameter of 0.26 mm), and the like that are commercial products can be adopted.

In addition, it is preferable to form a depressed portion (28), such as a groove, in the front end portion of the outer tube (11), for example, as shown in FIG. 1, when a tissue is collected under the guide of an image of a supersonic wave or an image of an ultrasonic endoscope. This is because the formation of the depressed portion (28) causes irregular reflection by a supersonic wave, allows the front end portion of the outer tube (11) to be clearly drawn on an image, and facilitates confirmation of the exact position of the front end portion of the outer tube (11) when a target body part or an organ is punctured. The depressed portion (28) just has to be able to reflect a supersonic wave irregularly, and can adopt any shape and structure, such as a concentric groove, a spiral groove, a recess, and an annular groove. In the case of a typical optical endoscope that does not use a supersonic wave, it is natural that it is not necessary to form the depressed portion (28) at the front end portion of the outer tube (11).

Additionally, it is necessary to make the length of the outer tube (11) larger than at least the length of the endoscope because manipulation is made through the inside of the endoscope, for example, a tissue sample is collected under endoscope observation. Additionally, it is natural that a length capable of reaching a target part is required. Even in respect of this length, the commercial puncture needle can be used as described above, and 120 cm to 200 cm are typically recommended. Additionally, for example, when a puncture is made from the outside directly under typical ultrasonic observation without using an endoscope to collect a tissue sample, the length of the outer tube (11) may be determined if needed, and for example, in commercial puncture needles, the outer tube (11) may be adopted as effective length about 75 to 200 mm.

(2) Inner Rod

When a target body part or organ is punctured from the outside of the body, the inner rod (23) prevents tissues other than a target part, such as a target body part, from entering the outer tube (11), and is switched to the closing posture (S) in which the inner rod is located closer to the middle side than the front end of the outer tube (11) inside the outer tube (11). Additionally, in puncture manipulation, when the outer tube (11) has arrived at a predetermined position of a target body part or organ, it is necessary to switch the inner rod (23) to the removal posture (R) to push put the inner rod in order to remove the foreign matter that has entered the outer tube when the outer tube (11) has passed through other parts until then. For this reason, a circular rod shape having a flat front end is preferable as the shape of the inner rod (23). Additionally, it is naturally necessary to make the length of this inner rod (23) larger than the total length of the outer tube (11), and it is recommended that the length of the inner rod is made several centimeters larger than the total length of the outer tube (11) in consideration of the operability of the inner rode. Moreover, it is natural that the external diameter of the rod (23) should be smaller than the internal diameter of the outer tube (11) to be used. In addition, in one embodiment of the present invention, a commercial inner rod (23) corresponding to the relevant puncture needle (2) can be used.

(3) Stopper member

The stopper member (12) stops a collected sample (tissue) suctioned into the outer tube (11) at the front end thereof at the time of sampling (tissue collection), and a tissue of a desired size (length) can be collected by setting the separation distance between the front end position of the stopper member (12) and the front end position of the outer tube (11). Additionally, by adjusting this separation distance, it is possible to flexibly cope with the size of a target body part or organ or the thickness thereof in a puncture direction. Since the collected sample enters the outer tube (11) only to the front end portion of the stopper member (12), tissue crushing can be suppressed without receiving a excessive dynamic impact by suction or negative pressure.

The clearance between an outer peripheral surface of the stopper member (12) and the inner peripheral surface of the outer tube (11) is determined on the basis of the following factors.

(1) Clearance such that insertion into the outer tube (11), and pull-out from the inside of the outer tube (11) (detachment act) can be smoothly performed without resistance.

(2) If the clearance is too large, since the negative pressure effect exerted by suction is small at the time of suction by the suction device (21), a tissue cannot be sufficiently suctioned.

(3) If the clearance is too narrow, sliding resistance with the inner surface of the outer tube (11) becomes large, and smooth advancing and retreating manipulation is hindered.

(4) If the clearance becomes excessively narrow, strong resistance is generated against the suction and negative pressure manipulation by the suction device (21), and operability deteriorates. Additionally, an abrupt drop in internal pressure may be caused by the suction manipulation, abrupt suction of a tissue into the outer tube (11) may be caused, and tissue crushing may be caused.

It is also preferable to appropriately determine the external diameter of the stopper member (12) in consideration of the above clearances. However, for example, in the case of a rod-shaped stopper member, the stopper member just have to have the same size as the specification of the external diameter of the inner rod (23), and a commercial product corresponding to a puncture needle can be used. When the front end portion of the stopper member (12) is disk-shaped or column-shaped, the stopper member can be used if the maximum diameter thereof is the external diameter of the inner rod (23).

Although the shape of the stopper member (12) is not limited to a specific shape, for example, the stopper member may have, for example, a rod shape as a whole. In this case, the stopper member is also able to serve as the inner rod (23). In this case, the length that is sufficient to make the front end of the stopper member (12) inserted into the outer tube (11) protrude from the front end of the outer tube (11) as the inner rod (23) is naturally required.

Additionally, the shape of the stopper member (12) just has to give the front end portion of the stopper member that comes into contact with a collected sample a stopper mechanism for the suctioned sample. For example, the front end portion of the stopper member may be disk-shaped or column-shaped, and most of a portion behind the front end portion may be wire-shaped or the like. In this case, since a sufficient clearance can be secured between the outer tube (11) and the stopper member (12), the pressure fluctuation caused by excessively abrupt suction can be avoided, and dynamic tissue destruction can be suppressed by gentle suction manipulation.

At this time, the wire-shaped portion needs to have the strength such that a front end portion thereof can be inserted into a predetermined part within the outer tube (11), that is, the strength such that the front end portion can be inserted without buckling against sliding resistance with the inner surface of the outer tube (11) generated at the time of insertion.

If the front end shape of the stopper member (12) is acute-angle-shaped, this is preferable because implementation can be made at low costs, and if the front end shape is disk-shaped or column-shaped, this is preferable because a suctioned sample is reliably stopped.

On the other hand, if indications, such as the scales (20), are appended on the base end (external terminal) side of the stopper member (12) as mentioned above, since the separation distance from the front end portion of the outer tube (11) to the front end portion of the stopper member (12) can be grasped by indications, such as the scales (20), this is preferable.

In addition, a flute or a spiral groove may be provided along a length direction in the outer peripheral surface of the stopper member (12). Thereby, even if the clearance between the outer peripheral surface of the stopper member (12) and the inner peripheral surface of the outer tube (11) is small, the passage cross-sectional area of the ventilation passage (14) can be made large, the resistance within the tube at the time of suction can be suppressed, and smooth suction manipulation can be performed.

Although the size of the stopper member (12) is set according to the internal diameter of an outer tube (11), the diameter is preferably set so as to suit the factors that determine the clearance. That is, if the size of this stopper member (12) is excessively small as compared to the internal diameter of the outer tube (11), since the space within the outer tube (11) becomes large, there is a possibility that the suction force using the suction device (21) may decrease, and a sufficient amount of tissue cannot be collected by one suction, and there is a possibility that a collected tissue or sample may be scattered or destroyed due to strong suction.

On the other hand, when the stopper member (12) is excessively thick and the clearance with the inner surface of the outer tube (11) is narrow, the space volume within the outer tube (11) decreases, and the inside of the sample containing portion (13) is greatly decompressed by a slight suction manipulation. As a result, a sample tissue is abruptly suctioned by a strong force and collides with or come into contact with the inner surface of the stopper member (12) or the outer tube (11) violently. Thus, there is possibility that tissue destruction may be caused.

Additionally, as for the length of the stopper member (12), it is preferable that a portion exposed to the outside of the connecting portion (15) is secured to such a degree that an operator can perform manipulation, such as alignment by upward and downward movement when the stopper member is disposed at a predetermined position within the outer tube (11) even in a state where the connecting portion (15) is mounted. Particularly, when the scales (20) or the like are additionally provided on the base end side in order to flexibly change the size (length) of a collected sample, the length of the sample that can be exposed to the outside of the connecting portion (15) so that the scales or the like can be clearly read is secured.

(4) Connecting Portion

The connecting portion (15) is a member that connects the suction device (21) that suctions and decompresses the inside of the outer tube (11), allows the stopper member (12) to be inserted thereinto, and is connected to the base end portion of the outer tube (11). Although the connecting portion (15) is a member separate from the outer tube (11) in this embodiment, in the invention, the connecting portion may be integrally formed at the base end portion of the outer tube (11). In this case, the connecting portion (15) is provided with the stopper member insertion port (17) and the suction device communication port (18).

The connecting portion (15) just has to include the stopper member insertion port (17), the suction device communication port (18), and the outer tube connection port (16) that are opened. Specifically, although trident tubes, such as a T-shaped tube and a Y-shaped tube, are preferable as the connecting portion, the shape of the connecting portion is not limited to a specific shape. Although the dimension of the connecting portion (15) can be appropriately determined according to the external diameter of the outer tube (11), the specification of suction device (21), the specification of the stopper member (12), or the like, when easiness of joining each member is taken into consideration, for example, the external diameter of the suction device communication port (18) is preferably approximately equal to the external diameter of a conjugation tube of the suction device (21). Moreover, it is necessary that the internal diameter of the connecting portion (15) is set to a size such that the stopper member (12) can pass smoothly through at least the portion through which the stopper member (12) passes. Specifically, it is preferable that the internal diameter of the connecting portion (15) in the portion through which that the stopper member (12) passes be equal to or larger than at least the internal diameter of the outer tube (11).

The connection between the suction device communication port (18) and the suction device (21) can be made by joining using a joining instrument that can withstand pressure reduction, for example, a proof-pressure tube, a joining union joint, or the like, or screwing of a joining portion of the suction device (21) into the suction device communication port (18). This joining portion is airtightly is connected so that leaking at the time of suction or pressure reduction can be prevented and a pressure-reduced state inside the puncture needle can be held at the time of sampling.

The connection between the outer tube connection port (16) and the base end portion of then outer tube (11) is also joined by the same technique as the suction device communication port (18), and an airtight state is held.

The connecting portion (15) is structured so that the stopper member (12) can be inserted into the outer tube (11) from the stopper member insertion port (17), and the stopper member insertion port (17) is airtightly held. As this airtight holding structure, for example, joining by a variant union joint that can join portions having mutually different external diameters or an airtight stopper provided around a through hole that allows the stopper member (12) to pass therethrough while maintaining sealing performance, or the like is illustrated.

In the stopper member insertion port (17), a joining method in which a measure that can change the insertion depth position of the stopper member (12) is taken is recommended. Specifically, when the airtight stopper is used, the stopper is configured so that slip of a contact portion with the stopper member (12) is improved, the advancing and retreating motion of the stopper member (12) is allowed, the separation distance between the front end of the outer tube (11) and the front end of the stopper member (12) can be adjusted, and the size (length) of a collected sample can be flexibly adjusted. In addition, the adjustment of the size of this collected sample can also be linked with the size of the internal diameter of the outer tube (11), can flexibly change the amount or the like of a collected tissue, and can improve the Trucut method as a conventional tissue collection method.

(5) Suction Device

In sampling manipulation, the suction device (21) is connected to the suction device communication port (18) of the connecting portion (15), and is used in order to reduce the pressure within the outer tube (11) by suction, exhaust, or the like.

In addition, in this embodiment, the injector type suction device (21) is used as the suction device, and the inside of the outer tube (11) can be brought into a pressure reduction state by pulling back a plunger within the suction device. However, if the suction device (21) to be used in one embodiment of the present invention is a device that can decompress the inside of the outer tube (11) to apply negative pressure to the sample containing portion (13), for example, any instrument or device, such as an exhaust pump, may be adopted.

As these suction devices or other suction device, it is also recommended that a pressure gauge or the like is installed in order to prevent destruction or the like of a collected tissue. Additionally, in order to prevent an abrupt drop in pressure within the sample containing portion (13) and to avoid dynamic damage of a collected tissue, it is also preferable to connect and attach a pressure adjustor to the suction device in parallel with the suction device. As this pressure adjustor, any pressure adjustors that can adjust the exhaust velocity within the outer tube (11) may be used, for example, a leak valve or the like can be used.

Next, a method of collecting a tissue using the suction puncture device will be described.

Figure 3A:
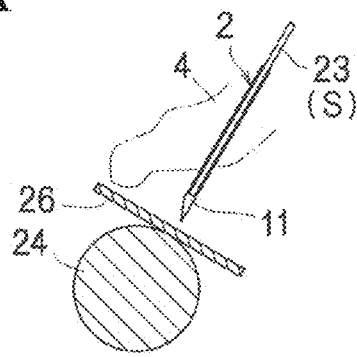
FIG. 3A is a schematic view illustrating a procedure of a suction puncture method of one embodiment of the present invention.

First, the ultrasonic endoscope (4) is used to draw a target body part or organ (simply referred to as a target body part in order to simplify description) on an echo screen. After a line that is easiest to make a puncture identified, the color Doppler is used together to confirm that there is no interposed blood vessel on the puncture line, and the position of the ultrasonic endoscope (4) is fixed. Next, the puncture needle (2) is mounted within the ultrasonic endoscope (4), and the front end of the puncture needle (2) is taken out from the forceps port (9) of the endoscope (4). The puncture needle (2) includes the outer tube (11), and the inner rod (23) arranged instead of the stopper member (12) inside the outer tube. The inner rod (23) is held in the closing posture (S) in which the inner rod is located at a position as closer to the front end portion as possible slightly inside a front end port of the outer tube (11). As shown in FIG. 3A, the puncture needle (2) in this state is guided to the vicinity of the target body part (24) under the guide of the ultrasonic endoscope (4).

Figure 3B:
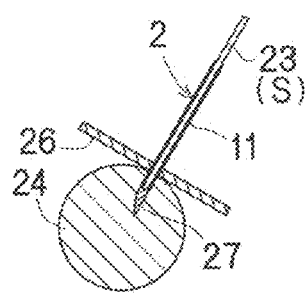
FIG. 3B is a schematic view illustrating the procedure of the suction puncture method of one embodiment of the present invention.
Figure 3C:
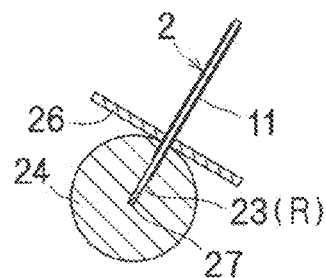
FIG. 3C is a schematic view illustrating the procedure of the suction puncture method of one embodiment of the present invention.

Next, while seeing the echo screen under the ultrasonic endoscope guide, as shown in FIG. 3B, for example, an affected predetermined part of the target body part (24) is punctured by the tip of the puncture needle (2). If the puncture needle (2) reaches a predetermined part, tissues (27) other than the target part, such as an alimentary canal mucosa (26), may enter the inside of the front end of the outer tube (11). Thus, as shown in FIG. 3C, the inner rod (23) is switched to the removal posture (R) in which the inner rod is pushed out further forward than the front end of the outer tube (11), and the other tissues (27) accumulated inside the outer tube (11) are discharged.

Figure 3D:
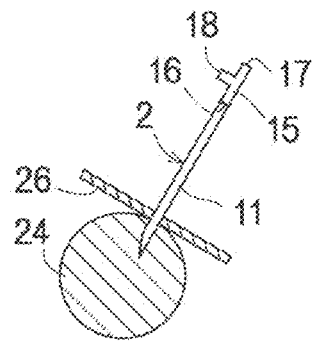
FIG. 3D is a schematic view illustrating the procedure of the suction puncture method of one embodiment of the present invention.

Next, the inner rod (23) is extracted from the base end of the outer tube (11), and as shown in FIG. 3D, the outer tube connection port (16) of the connecting portion (15) is connected to the base end of the outer tube (11). In addition, in this embodiment, the connecting portion (15) is attached after the inner rod (23) is taken out. However, if the inner rod (23) is sufficiently long, the connecting portion (15) may be attached to the base end of the outer tube (11) in advance. In this case, the inner rod (23) is inserted through the stopper member insertion port (17).

Figure 3E:
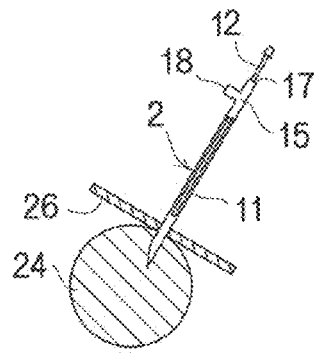
FIG. 3E is a schematic view illustrating the procedure of the suction puncture method of one embodiment of the present invention.
Figure 3F:
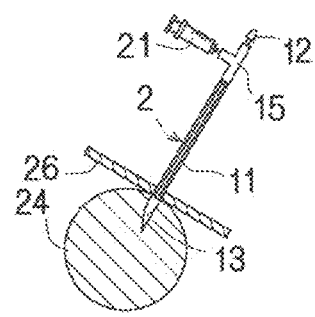
FIG. 3F is a schematic view illustrating the procedure of the suction puncture method of one embodiment of the present invention.

Next, as shown in FIG. 3E, the stopper member (12) is inserted into the outer tube (11) from the stopper member insertion port (17), and as shown in FIG. 3F, the front end of the stopper member (12) is arranged and held at a position separated from the front end by a predetermined distance within the outer tube (11). The sample containing portion (13) is formed between the front end of the stopper member (12) and the front end of the outer tube (11), and the length of the sample containing portion (13) becomes the length of a required sample. Accordingly, the length (thickness) of a tissue sample in the depth direction can be adjusted and collected depending on the position of this stopper member (12). In addition, the ventilation passage (14) is formed between the outer peripheral surface of the stopper member (12) and the inner surface of the outer tube (11).

Figure 3G:
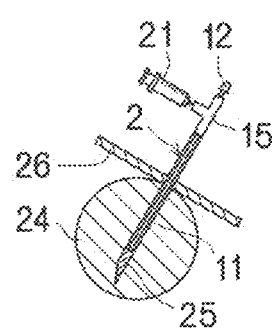
FIG. 3G is a schematic view illustrating the procedure of the suction puncture method of one embodiment of the present invention.

Next, as shown in FIG. 3F, the suction device (21) is connected to the suction device communication port (18), the cock (22) is opened, and negative pressure is applied to the sample containing portion (13) via the ventilation passage (14) by the suction of the suction device (21). If the negative pressure is applied to the sample containing portion (13), the cock (22) is closed to hold the negative pressure. In this state, as shown in FIG. 3G, the front end portion of the outer tube (11) is advanced to a predetermined part of the target body part (24), and a portion of the predetermined part is cut off and collected by the front end edge of the outer tube (11). The cut-off collected substance (25) is contained in the sample containing portion (13) by the negative pressure in a tissue state.

Figure 3H:
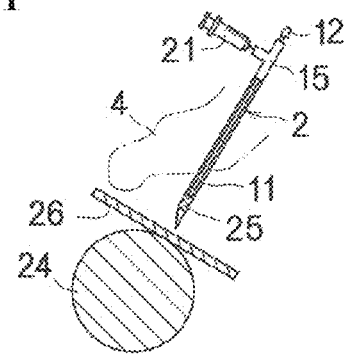
FIG. 3H is a schematic view illustrating the procedure of the suction puncture method of one embodiment of the present invention.

Thereafter, the negative pressure is released, and as shown in FIG. 3H, the puncture needle (2) is quickly extracted from the ultrasonic endoscope (4), the collected substance (25) contained in the sample containing portion (13) is taken out to a laboratory dish, and is used as a sample for tissue testing.

Figure 4:
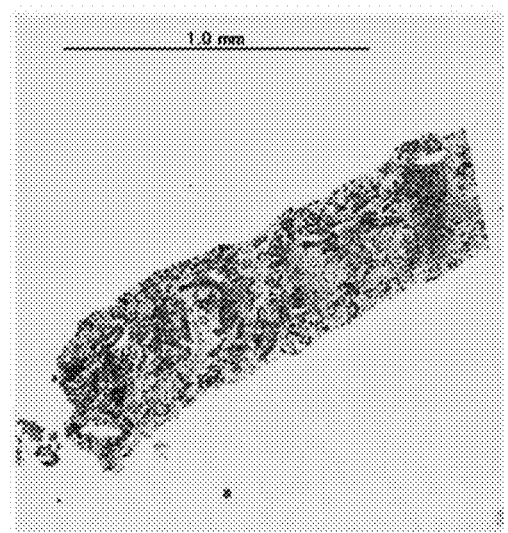
FIG. 4 is a photograph of a collected substance collected from a pancreatic cancer using the suction puncture device of the invention.

A photograph of a collected substance of which a tissue is collected under the guide of the ultrasonic endoscope with respect to, specifically, a pancreatic cancer using the suction puncture device (1) is shown in FIG. 4. As shown in this FIG. 4, according to the suction puncture device of one embodiment of the present invention, a neat elongated tissue piece can be collected, and not only molecular biology diagnosis but also tissue diagnosis can be adequately performed.

Figure 5:
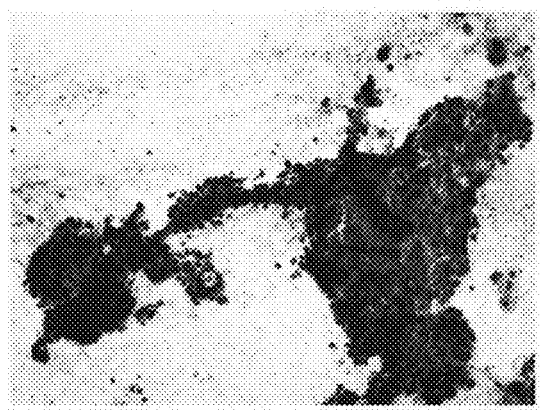
FIG. 5 is a photograph of a collected substance collected from a pancreatic cancer using a conventional suction puncture device.
Figure 6:
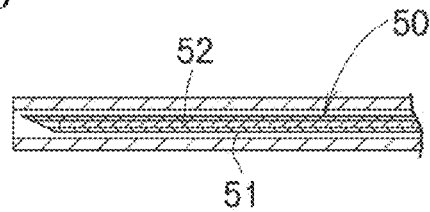
FIG. 6 is a cross-sectional view of a puncture needle tip used for a conventional suction method.
Figure 7A:
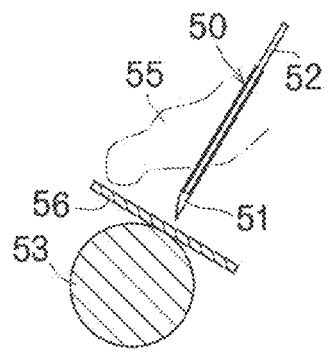
FIG. 7A is a schematic view illustrating a procedure of the conventional suction method.
Figure 7B:
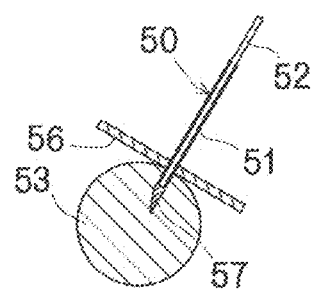
FIG. 7B is a schematic view illustrating the procedure of the conventional suction method.
Figure 7C:
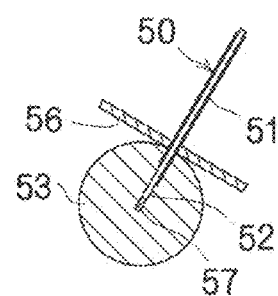
FIG. 7C is a schematic view illustrating the procedure of the conventional suction method.
Figure 7D:
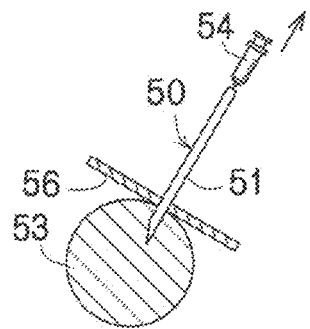
FIG. 7D is a schematic view illustrating the procedure of the conventional suction method.
Figure 7E:
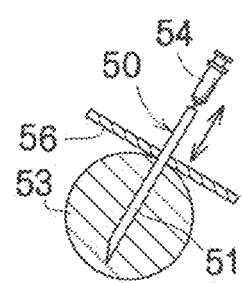
FIG. 7E is a schematic view illustrating the procedure of the conventional suction method.
Figure 7F:
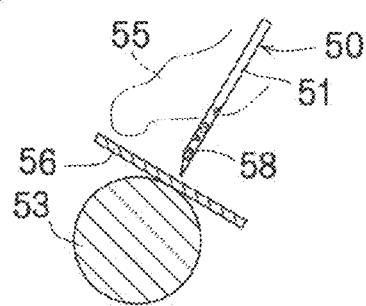
FIG. 7F is a schematic view illustrating the procedure of the conventional suction method.
Figure 8:
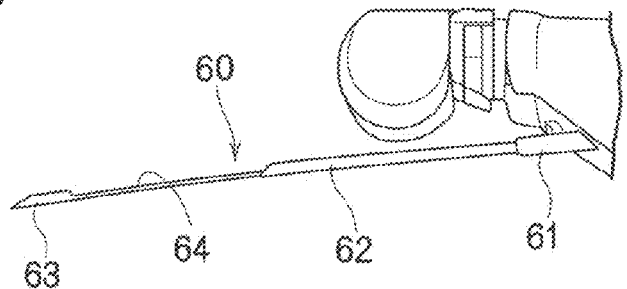
FIG. 8 is an appearance view of a puncture needle tip used for a conventional Trucut method.
Figure 9A:
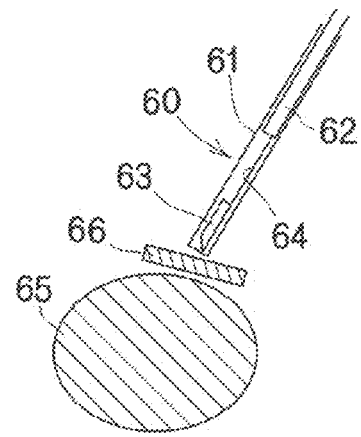
FIG. 9A is a schematic view illustrating a procedure of the conventional Trucut method.
Figure 9B:
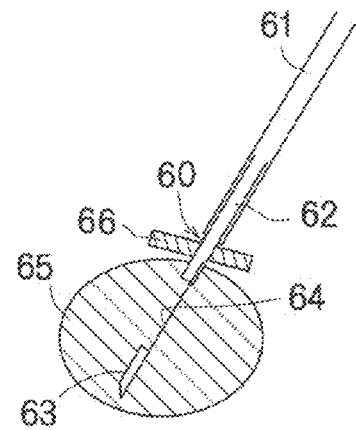
FIG. 9B is a schematic view illustrating the procedure of the conventional Trucut method.
Figure 9C:
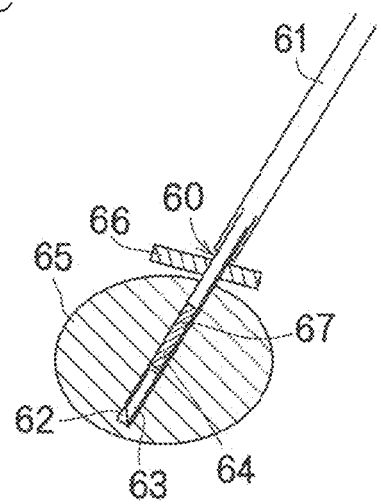
FIG. 9C is a schematic view illustrating the procedure of the conventional Trucut method.
Figure 9D:
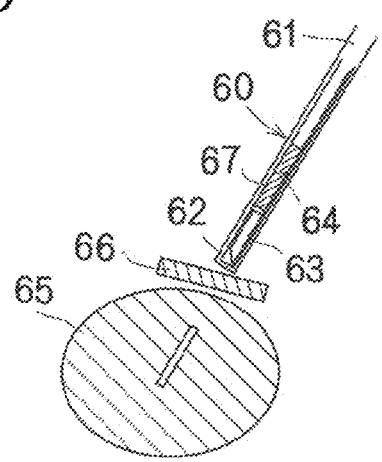
FIG. 9D is a schematic view illustrating the procedure of the conventional Trucut method.

In contrast, when a tissue is collected under the guide of the ultrasonic endoscope with respect to the same pancreatic cancer by the aforementioned conventional suction puncture device, as shown in FIG. 5, a tissue is scattered, and a tissue piece cannot be collected. For this reason, tissue diagnosis is difficult, an obtained and collected substance becomes an extremely small amount of a sample as well as cell diagnosis is brought about, and molecular biology diagnosis from the sample is also difficult.

In the above embodiment, the puncture needle is used so as to be inserted into the ultrasonic endoscope. For this reason, in a typical optical endoscope, if even body parts that cannot be directly and optically observed are body parts or organs that can be observed by a supersonic wave in a part where the ultrasonic endoscope can reach, tissues or cells can be collected from a target body part or the like under the guide of the ultrasonic endoscope by the suction puncture device of one embodiment of the present invention.

For example, when an body part, such as the kidney, that is directly invisible and cannot be observed by an optical endoscope is targeted, the ultrasonic endoscope mounted with the suction puncture device of one embodiment of the present invention is inserted to the inside of the stomach, an image of the target body part is obtained by ultrasonic imaging at a stomach inner wall, a required predetermined part is punctured by the guide of this image, and a tissue or the like is suctioned and collected. As the target body parts or organs in this case, the pancreas, a mediastinal tumor, a lymph node, an alimentary canal submucosal tumor, and the like are illustrated in addition to the kidney.

However, one embodiment of the present invention is not limited to the apparatus or method mounted and used as to pass through the ultrasonic endoscope.

For example, when a target body part or the like can be observed from the outside of the body with a supersonic wave or depending on cases, with X rays, and when there are no other body parts to hinder when a puncture is made by the puncture needle, it is necessary to use neither the ultrasonic endoscope nor the typical optical endoscope. In this case, under the guide of a typical ultrasonic (echo) image or an X-ray image, a puncture is directly made from the outside of the body by the puncture needle of the suction puncture device of one embodiment of the present invention, and tissues or cells are collected from a predetermined par of the target body part. As the target body parts in this case, for example, the liver, the kidney, the pancreas, and the like are illustrated. However, in the case of the pancreas, the target body part is limited to a part that can be observed with an echo from the outside of the body.

Additionally, if a target body part or the like is an observable body part or organ of which the image is directly projected by a typical optical endoscope, the suction puncture device of one embodiment of the present invention may be used so as to be mounted in a state where the device passes through the optical endoscope. In this case, the suction puncture device of one embodiment of the present invention includes the same structure as a case where the device is used for an ultrasonic endoscope, and is manipulated under the guide of this optical endoscope to collect tissues or cells from the target body part or the like. However, since the collection is made within an optical visible range, the puncture needle does not need to protrude so long from the terminal of the endoscope. As the target body parts in this case, for example, the stomach, the duodenum, the esophagus, the large intestine, and the like are illustrated.

The suction puncture method and suction puncture device that are described in the above embodiment are illustrated in order to embody the technical idea of one embodiment of the present invention. The shapes, dimensions, quality, structure, arrangement, operating procedure, and the like of the respective members are not limited to those of this embodiment, and various changes can be made within the claims of one embodiment of the present invention. Various modifications of the suction puncture device of the invention will be described below.

In the suction puncture device of one embodiment of the present invention, it has already been described that the scales are used indexes for adjustment of the volume of the sample containing portion when the scales are provided on the base end side of the stopper member. However, the index portion for the volume adjustment is not limited to the above-described scales, and various configurations can be taken.

Figure 10:
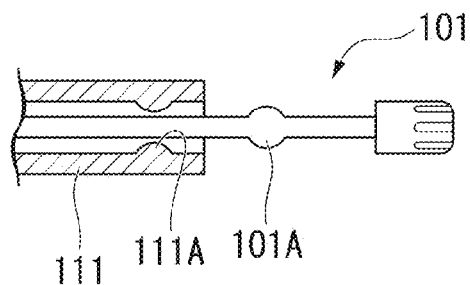
FIG. 10 is a schematic view showing a base end portion of a stopper member in a modified example of one embodiment of the present invention.

In a modification shown in FIG. 10, a larger-diameter portion 101A that is formed such that the radial maximum dimension is larger than other parts is formed on the base end side of the stopper member 101 as the index portion, and an inner cavity of stopper member insertion port 111 is formed with a smaller-diameter portion 111A in which the internal diameter is reduced. Thereby, since a click feeling is generated when the larger-diameter portion 101A rides over the smaller-diameter portion 111A, an operator can use this click feeling as an index for volume adjustment of a sample containing portion.

Figure 11:
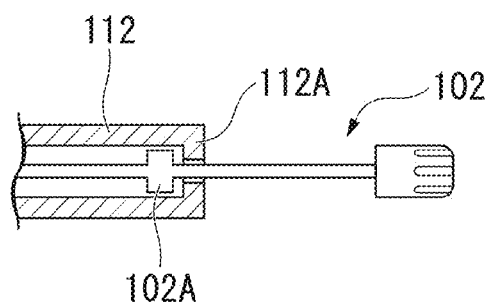
FIG. 11 is a schematic view showing a base end portion of a stopper member in a modified example of one embodiment of the present invention.

In a modification shown in FIG. 11, a flange 102A that protrudes in the radial direction is formed on the stopper member 102 as the index portion, and the diameter of an opening of a base end portion 112A of a stopper member insertion port 112 is reduced to such a degree that the flange 102A is not overridden. Thereby, when the volume of a sample containing portion becomes a predetermined size, since the flange 102A comes into contact with the base end portion 112A of the stopper member insertion port 112, and the stopper member 102 cannot be retreated any more with respect to the outer tube. Accordingly, the flange 102A can be used as an index for volume adjustment of the sample containing portion. In addition, since the stopper member 102 cannot be extracted in this case, the flange is also preferably used as the inner rod.

Figure 12:
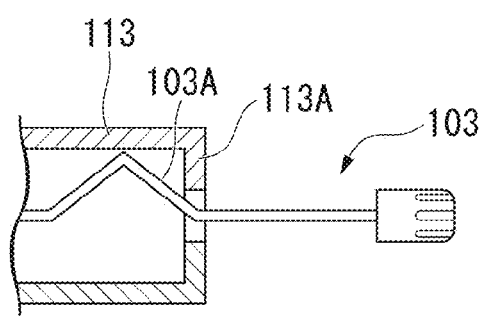
FIG. 12 is a schematic view showing a base end portion of a stopper member in a modified example of one embodiment of the present invention.

In the modification shown in FIG. 12, a locking portion 103A that functions as the index portion is provided by bending the base end portion of the stopper member 103. Thereby, if the volume of a sample containing portion becomes a predetermined size, since the locking portion 103A comes into contact with a base end portion 113A of a stopper member insertion port 113 of which the diameter of an opening is reduced. Accordingly, the locking portion 103A can be used an index for volume adjustment of the sample containing portion. In this modification, it is possible to pull the stopper member 103 with a stronger force to elastic deform and extract the locking portion 103A after the locking portion 103A comes into contact with the base end portion 113A. Additionally, since the locking portion that functions as the index portion can be formed simply by bending the rod-shaped stopper member, there is also an advantage that manufacture is easy.

Figure 13:
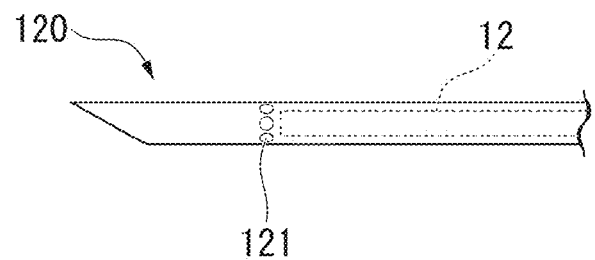
FIG. 13 is a schematic view showing a front end portion of an outer tube in a modified example of one embodiment of the present invention.

Additionally, as shown in FIG. 13, if the outer peripheral surface of an outer tube 120 corresponding to the front end position of the stopper members (the stopper member 12 is shown as an example in FIG. 13) specified by the above-described various indices is formed with an outer tube index 121 composed of a dimple that can be recognized by an ultrasonic image. Therefore, since the outer tube index 121 can be used as an indication for manipulation by the ultrasonic image, this configuration is preferable.

Additionally, although the example in which the stopper member and the inner rod are separate members has been described in the above embodiment, the same member may serve as the inner rod and the stopper member. In this case, since suction of a tissue cannot be performed unless the stopper member insertion port is airtightly sealed after the stopper member is retreated from the removal posture to form the sample containing portion, there is a concern that manipulation may become complicated.

Figure 14:
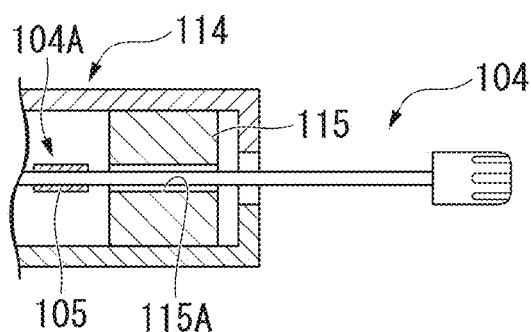
FIG. 14 is a schematic view showing a base end portion of a stopper member in a modified example of one embodiment of the present invention.

Thus, for example, as in a modification shown in FIG. 14, an annular elastic body 115 having a hole 115A at a base end portion of a stopper member insertion port 114, and a metallic tube 105 is attached to the stopper member 104 so as to form a larger-diameter portion 104A, of which the radial dimension is enlarged, in the stopper member 104. Moreover, the internal diameter of the hole 115A is set to be slightly larger than the external diameter of the parts of the stopper members 104 other than the larger-diameter portion 104A, and slightly smaller than the external diameter of the larger-diameter portion 104A.

Then, if the stopper member 104 is retreated to form the sample containing portion, a base end portion of the stopper member insertion port 114 that communicate with the stopper member insertion port is airtightly closed when the larger-diameter portion 104A enters the hole 115A while elastically deforming the elastic body 115, and the larger-diameter portion 104A is located in the hole 115A. As a result, a state where suction of a tissue is possible can be established simply by the manipulation of forming the sample containing portion, and a suction puncture device that is easier to manipulate can be obtained.

Additionally, if a tissue is reliably held by the front end of the stopper member, the clearance with the outer tube may become too small, and a suction force may not be efficiently transmitted to the sample containing portion. In order to eliminate this, the outer tube and the stopper member can be changed to various shapes. In addition, the clearance indicates a gap formed between the inner peripheral surface of the outer tube and the outer peripheral surface of the stopper member, and has a great influence on the volume of the ventilation passage.

Figure 15:
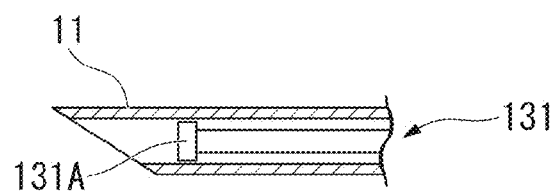
FIG. 15 is a schematic view showing a front end portion of a stopper member in a modified example of one embodiment of the present invention.

In a modification shown in FIG. 15, in a stopper member 131, the diameter on the base end side is made smaller than that of a front end portion 131A holding a tissue. Thereby, since a relatively large clearance can be secured closer to the base end than the front end portion 131A, a suction force can be efficiently transmitted to the sample containing portion. In such a case, it should be noted that the external diameter of a part on the base end side is set to have such a degree of rigidity that advancing and retreating manipulation can be reliably transmitted to the front end portion, without causing buckling or the like by the advancing and retreating manipulation of the stopper member.

Figure 16:
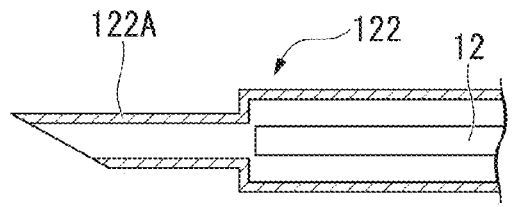
FIG. 16 is a schematic view showing a front end portion of an outer tube in a modified example of one embodiment of the present invention.

In a modification shown in FIG. 16, in an outer tube 122, the internal diameter on the base end side is made larger than the internal diameter of a front end portion 122A in which the sample containing portion is formed. Even in this way, the clearance on the base end side of the sample containing portion can be increased.

Figure 17:
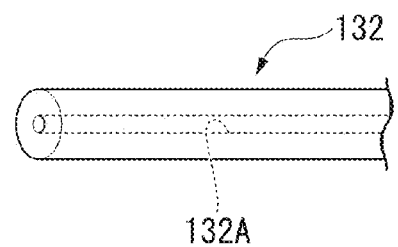
FIG. 17 is a schematic view showing a front end portion of a stopper member in a modified example of the invention one embodiment of the present invention.

In a modification shown in FIG. 17, a suction channel 132A that passes through a stopper member 132 in the longitudinal direction is formed. Although a suction force can be efficiently transmitted to the sample containing portion even in this way, a front end port of the suction channel 132A is preferably set to a size such that a collected tissue does not enter the suction channel 132A. The suction channel 132A may communicate with an opening formed in an outer peripheral surface of the stopper member in a longitudinal intermediate portion of the stopper member.

Figure 18A:
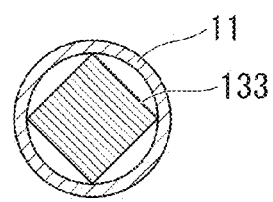
FIG. 18A is a cross-sectional view of an outer tube and a stopper member in a modified example of one embodiment of the present invention.
Figure 18B:
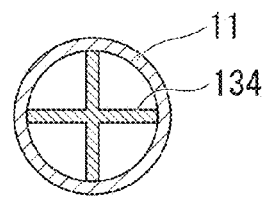
FIG. 18B is a cross-sectional view of an outer tube and a stopper member in a modified example of one embodiment of the present invention.

A modification shown in FIGS. 18A and 18B is an example in which the clearance is secured with the outer tube 11 of which the radial cross-sectional shape is circular by adopting the radial cross-sectional shape of the stopper member as a non-circular shape. The cross-sectional shape of the stopper member is not limited to a quadrangular shape as in a stopper member 133 shown in FIG. 18A and a cross form as in a stopper member 134 shown in FIG. 18B, and may be other non-circular shapes. Particularly, if the stopper member has a shape having about ten or less contact points (for example, the stopper member 133 has four contact points.) with the inner wall of the outer tube, and a portion between at least two contact points in a cross-section is formed linearly, the clearance can be efficiently increased.

Figure 19:
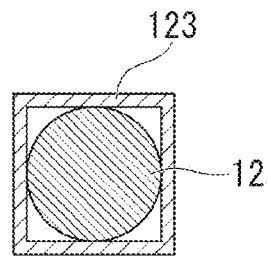
FIG. 19 is a cross-sectional view of an outer tube and a stopper member in a modified example of one embodiment of the present invention.

Moreover, as in a modification shown in FIG. 19, the clearance can be similarly increased even if it combines the outer tube 123 of which the radial cross-sectional shape is non-circular, and the stopper member 12 of which the cross-sectional shape is circular. That is, if the radial cross-sectional shape of one of the outer tube and the stopper member is made circular, and the radial cross-sectional shape of the other is non-circular, the clearance is efficiently increased. As a result, suction force can be efficiently transmitted to the sample containing portion.

In addition, even in these cases, similarly to a modification shown in FIG. 17, it is preferable to set a distal-end-side opening of a ventilation passage formed by a clearance to a size such that a suctioned and collected tissue does not enter.

Figure 20:
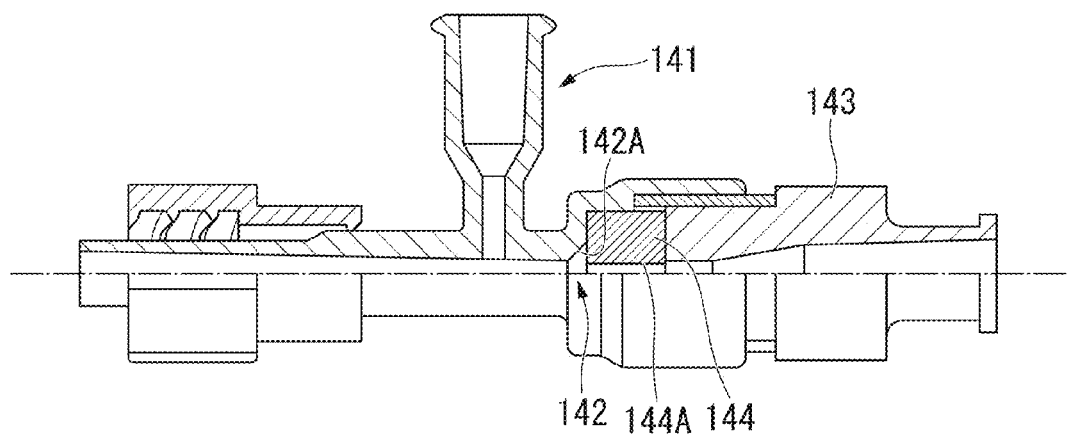
FIG. 20 is a view showing a portion of a connecting portion in a modified example of one embodiment of the present invention.

In the suction puncture device of one embodiment of the present invention, when a plurality of stopper members having different external diameters is properly used, the airtightness of the stopper member insertion port may not be easily maintained when a thinner stopper member is used. In this case, as in a modification shown in FIG. 20, a tapered portion 142A may be formed at a stopper member insertion port 142 of a connecting portion 141 so that the internal diameter becomes gradually smaller from an opening end, a doughnut-like elastic body 144 may be arranged between the stopper member insertion port 142 and a union joint 143, and the internal diameter of a hole 144A of the elastic body 144 may be set to be equal to or slightly smaller than the external diameter of the thickest stopper member.

Then, when a thin stopper member is used, the length of a portion where the union joint 143 connects with the connection portion 141 of the elastic body 144 is elongated, whereby the elastic body 144 is compressed in the direction of an axis, and a portion of the elastic body 144 enters the tapered portion 142A formed at the stopper member insertion port 142. As a result, the substantial internal diameter of the hole 144A is reduced, and an airtight state can be suitably secured even when a thin stopper member is used.

Additionally, it is needless to say that the suction device of one embodiment of the present invention may include a pressure adjusting device or a pressure gauge. Additionally, the respective configurations of the above described embodiment and respective modifications may be suitably combined together.

Finally, the results after the relationship between the clearance between the outer tube and the stopper member, and the certainty of tissue collection by suction is studied are shown.

Figure 21:
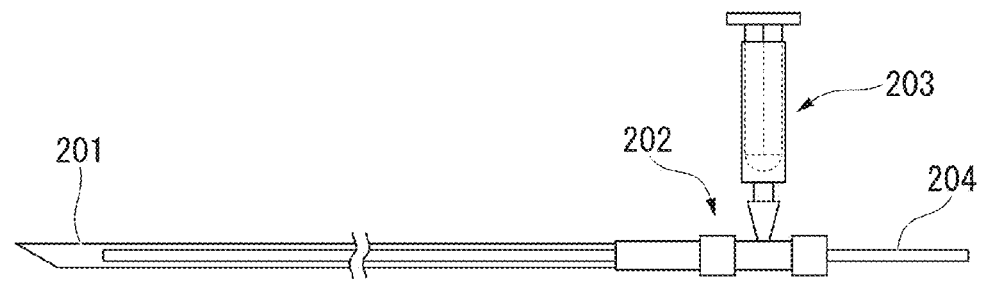
FIG. 21 is a schematic view of a mechanism used for an experiment in which the relationship between the clearance between an outer tube and a stopper member, and suction and collection of a tissue is studied.

The configuration of a mechanism used for study is schematically shown in FIG. 21. As an outer tube 201, a needle tube (the internal diameter of 0.92 mm and the total length of 1700 mm) of 19 gages was used, and a three-way cock 202 was airtightly connected to the base end. A syringe 203 with a maximum capacity of 60 ml was airtightly connected to one of the remaining two ports, and a stopper member 204 with a different external diameter was inserted from the other port. A rubber packing according to the diameter of a stopper member was attached to the port into which the stopper member 204 is inserted, and the airtightness of the port concerned was held in a state where the stopper member 204 is inserted.

As the stopper member, those having four kinds of sizes in which the external diameters are 0.45 mm (clearance of 0.47 mm (total of both)), 0.73 mm (clearance of 0.19 mm), 0.80 mm (clearance of 0.12 mm), and 0.85 mm (clearance of 0.07 mm) and all the external diameters are constant over the total length were prepared. Thus, in this study, the difference between the internal diameter of the outer tube and the external diameter of the stopper member was shown as clearance.

Suction and collection of a liver tissue was performed by puncturing the liver of a pig with the front end of the outer tube 201 of the above mechanism, and pulling a plunger of the syringe 203 only once up to 50 ml to apply negative pressure. Suction and collection was performed two or more times on the respective stopper members, and the amount of a tissue collected every time was measured. The results are shown in Table 1. In addition, in Table 1, the "clearance 0.92 mm" shows the result after suction and collection is performed by airtightly sealing the port into which the stopper member 204 of the three-way cock 202 is inserted, without using the stopper member 204 as a conventional method.

TABLE 1

| Clearance (mm) | Amount of Collection at First Puncture (mg) |
| --- | --- |
| 0.07 | 2.30 |
| 0.07 | 3.52 |
| 0.07 | 3.79 |
| 0.12 | 4.10 |
| 0.12 | 4.79 |
| 0.12 | 3.75 |
| 0.19 | 4.46 |
| 0.19 | 4.44 |
| 0.47 | 1.71 |
| 0.47 | 2.81 |
| 0.47 | 3.74 |
| 0.47 | 5.89 |
| 0.47 | 6.04 |
| 0.47 | 6.28 |
| 0.92 | 0.36 |
| 0.92 | 0.80 |
| 0.92 | 1.20 |
| 0.92 | 2.47 |
| 0.92 | 2.98 |
| 0.92 | 5.81 |
| 0.92 | 7.09 |

Figure 22:
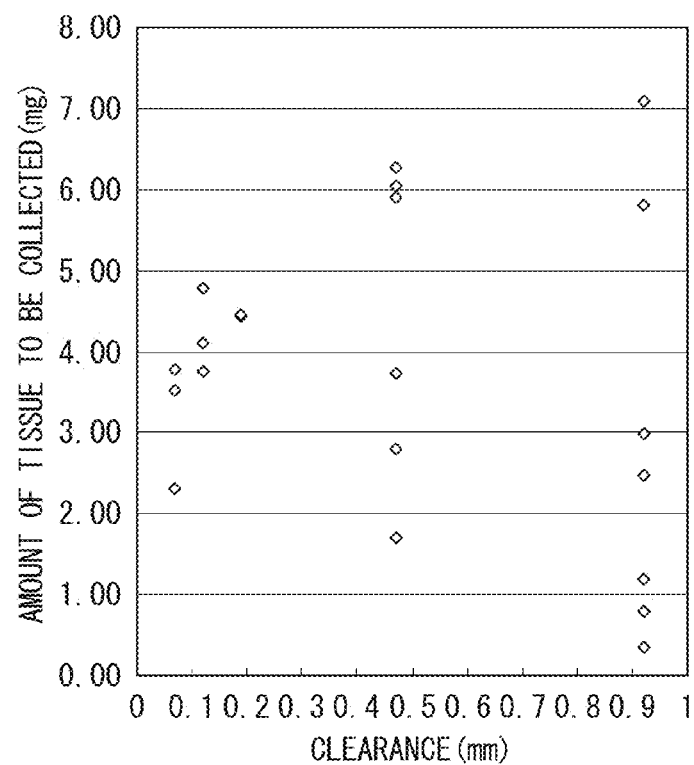
FIG. 22 is a graph showing the relationship between the clearance and the amount of a tissue to be collected.

In FIG. 22, the results of Table 1 are plotted by taking the amount of a tissue to be collected on the vertical axis, and taking the clearance on the horizontal axis. The tendency was observed in which the variation in the amount of a tissue to be collected becomes smaller as the clearance is smaller, and the variation in the amount of a tissue to be collected becomes larger as the clearance becomes larger.

Figure 23:
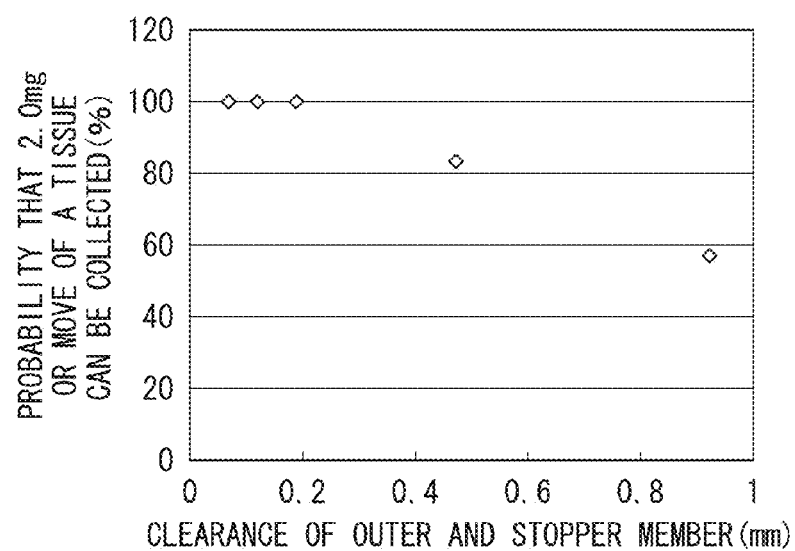
FIG. 23 is a graph showing the relationship between the probability at which a tissue of 2.0 mg or more can be collected, and the clearance.

Generally, if 2 mg or more of a tissue can be collected, tissue diagnosis is suitably performed using the tissue concerned. Therefore, the probability that 2 mg or more of a tissue can be collected by one suction and collection was studied for every clearance using the data of Table 1, and was shown in FIG. 23. As shown in FIG. 23, if the clearance is equal to or less than 0.2 mm, 2 mg or more of a tissue could be collected by one suction and collection with the probability of 100%. Additionally, even in the clearance 0.47 mm, 2 mg or more of a tissue could be collected by five of six suction and collection, and the probability was the high probability of 83.3%. In the conventional technique, it is said that the probability that 2 mg or more of a tissue can be collected by one suction and collection is from slightly less than 50 percent to less than 60 percent. However, it is shown that the amount of a tissue that tissue diagnosis is possible can be more reliably collected by one puncture and suction manipulation by performing suction while properly keeping the clearance with the outer tube using the stopper member. Accordingly, in the suction puncture device one embodiment of the present invention, it is expected that an increase in the invasion of a patient by redoing or the like of puncture and suction can be suitably suppressed.

While preferred embodiments of the present invention have been described above, these are not limitative of the invention. Additions, omissions, substitutions, and other modifications can be made without departing from the spirit or scope of the present invention. Accordingly, the present invention is not to be considered as being limited by the foregoing description, and is only limited by the scope of the appended claims.

The present invention includes the following technical idea.

(Supplementary Notes, Item 1)

A suction puncture device comprising:

a puncture needle having an outer tube that has an opening edge of a first front end formed in the shape of a blade, and a stopper member that has a second front end disposed within the outer tube at a position separated from the first front end of the outer tube by a predetermined distance;

a sample containing portion formed between the second end of the stopper member and the first front end of the outer tube;

a ventilation passage formed around the stopper member within the outer tube; and a suction unit connected to a first base end side of the outer tube, and communicated with the sample containing portion via the ventilation passage, wherein the outer tube has a connecting portion including a stopper member insertion port which allows the stopper member to be airtightly inserted thereinto and a suction unit communication port which allows the suction unit to be airtightly connected thereto on the first base end side;

the stopper member has a larger-diameter portion of which the radial dimension is enlarged, at a portion thereof in the longitudinal direction;

an annular elastic body is arranged in the stopper member insertion port so as to allow the stopper member to be inserted through the insertion port; and the stopper member insertion port is airtightly closed in a state where the larger-diameter portion is located within a hole of the elastic body.

(Supplementary Notes, Item 2)

The suction puncture device according to item 1, wherein the stopper member has an index portion that becomes an index of the volume of the sample containing portion.

(Supplementary Notes, Item 3)

The suction puncture device according to item 1, wherein the index portion is scales formed in the stopper member.

(Supplementary Notes, Item 4)

The suction puncture device according to item 1, wherein the index portion is a larger-diameter portion formed in the stopper member.

(Supplementary Notes, Item 5)

The suction puncture device according to item 1, wherein the index portion is a locking portion formed by curving a second base end side of the stopper member; and when the volume of the sample containing portion becomes a predetermined value, the retreat of the stopper member with respect to the outer tube is hindered by the locking portion.

(Supplementary Notes, Item 6)

The suction puncture device according to item 1, wherein an outer tube index capable of being visually recognized by an ultrasonic image is formed at an outer peripheral surface of the outer tube at a position corresponding to the position of the second front end of the stopper member when the volume of the sample containing portion has a predetermined value.

(Supplementary Notes, Item 7)

The suction puncture device according to item 1, wherein the stopper member is formed to have a smaller diameter closer to the second base end side than the second front end side.

(Supplementary Notes, Item 8)

The suction puncture device according to item 1, wherein the stopper member has a suction channel that penetrates in a longitudinal direction.

(Supplementary Notes, Item 9)

The suction puncture device according to item 1, wherein the outer tube is formed to have a larger internal diameter closer to the first base end side than on the first front end.

(Supplementary Notes, Item 10)

The suction puncture device according to item 1, wherein the outer tube and the stopper member has a circular cross-sectional shape in one radial direction, and a non-circular cross-sectional shape in the other radial direction.

(Supplementary Notes, Item 11)

The suction puncture device according to item 1, wherein the difference between the internal diameter of the outer tube and the external diameter of the stopper member is equal to or more than 0.05 mm and equal to or less than 0.5 mm.

What is claimed is:

1. A suction puncture device comprising: a tubular body having a distal edge defining a puncture needle, the distal edge further defining an opening at a distal end of the tubular body; a stopper member capable of advancing and retracting in a longitudinal direction within an interior of the tubular body to vary a distance between a distal end of the stopper member and the distal end of the tubular body, a ventilation passage being formed between an exterior surface of the stopper member and an interior surface of the tubular body; and a seal disposed in the tubular body and configured to seal the ventilation passage at a proximal end of the tubular body for less than a full movement range of the stopper member in the longitudinal direction; wherein a variable volume sample containing portion is formed within the interior of the tubular body between the distal end of the stopper member and the distal end of the tubular body wherein the seal comprises: the stopper member having a larger-diameter portion disposed within the tubular body and movable with the stopper member, a dimension of the larger-diameter portion being enlarged at a portion of the stopper member in a longitudinal direction; and an elastic body arranged in the tubular body so as to allow the stopper member to advance and retract through a hole included in the annular elastic body; wherein when the stopper member is retracted in a proximal direction by a predetermined distance, the larger-diameter portion locates within at least a portion of the hole of the elastic body to seal the ventilation passage.

2. The suction puncture device according to claim 1, wherein the tubular body includes a stopper member insertion port capable of fixing and holding a proximal end side of the stopper member at an arbitrary position.

3. The suction puncture device according to claim 2, wherein the connection port is capable of being airtightly connected with an end portion of the tubular body.

4. The suction puncture device according to claim 1, further comprising an opening and closing unit which is arranged between a suction unit and an end of the tubular body, and is capable of opening and closing fluid communication between the suction unit and the ventilation passage.

5. The suction puncture device according to claim 4, wherein the suction unit includes a pressure adjusting unit capable of adjusting a pressure change in the sample containing portion.

6. The suction puncture device according to claim 1, further comprising a protective tube covering the tubular body.

7. The suction puncture device according to claim 1, wherein the tubular body is mounted within an endoscope so as to be able to advance and retreat.

8. The suction puncture device according to claim 7, wherein the endoscope is an ultrasonic endoscope.

9. The suction puncture device according to claim 1, wherein the larger-diameter portion and hole are cylindrical.

* * * * *